United States Patent
Polzin et al.

(10) Patent No.: US 8,330,961 B1
(45) Date of Patent: Dec. 11, 2012

(54) OPTICAL MULTI-SPECIES GAS MONITORING SENSOR AND SYSTEM

(75) Inventors: Kurt A. Polzin, Owens Cross Roads, AL (US); Valentin Korman, Huntsville, AL (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 405 days.

(21) Appl. No.: 12/837,173

(22) Filed: Jul. 15, 2010

(51) Int. Cl.
*G01B 9/02* (2006.01)

(52) U.S. Cl. ...................................... 356/477

(58) Field of Classification Search ............... 356/451, 356/477, 480, 454, 519, 481, 450
See application file for complete search history.

(56) References Cited

U.S. PATENT DOCUMENTS

| | | | |
|---|---|---|---|
| 3,973,134 A * | 8/1976 | Begley et al. ............... | 250/574 |
| 7,059,766 B2 | 6/2006 | Lemoine et al. | |
| 7,559,701 B2 | 7/2009 | Knobloch et al. | |
| 7,684,656 B2 | 3/2010 | Chen | |
| 7,684,657 B2 | 3/2010 | Donlagic et al. | |
| 2002/0041723 A1 | 4/2002 | Ronnekleiv et al. | |
| 2002/0041724 A1 | 4/2002 | Ronnekleiv et al. | |
| 2003/0189711 A1 * | 10/2003 | Orr et al. ...................... | 356/484 |
| 2008/0219618 A1 | 9/2008 | McCarthy et al. | |
| 2008/0236747 A1 * | 10/2008 | Matsudo et al. ........ | 156/345.24 |
| 2009/0199630 A1 | 8/2009 | DiFoggio et al. | |
| 2009/0279583 A1 | 11/2009 | Hampson et al. | |
| 2010/0064785 A1 | 3/2010 | Kummer et al. | |
| 2010/0069785 A1 | 3/2010 | Arkwright et al. | |

* cited by examiner

*Primary Examiner* — Tarifur Chowdhury
*Assistant Examiner* — Jonathon Cook
(74) *Attorney, Agent, or Firm* — Peter J. Van Bergen; James J. McGroary

(57) ABSTRACT

The system includes at least one light source generating light energy having a corresponding wavelength. The system's sensor is based on an optical interferometer that receives light energy from each light source. The interferometer includes a free-space optical path disposed in an environment of interest. The system's sensor includes an optical device disposed in the optical path that causes light energy of a first selected wavelength to continue traversing the optical path whereas light energy of at least one second selected wavelength is directed away from the optical path. The interferometer generates an interference between the light energy of the first selected wavelength so-traversing the optical path with the light energy at the corresponding wavelength incident on the optical interferometer. A first optical detector detects the interference. At least one second detector detects the light energy at the at least one second selected wavelength directed away from the optical path.

24 Claims, 1 Drawing Sheet

OPTICAL MULTI-SPECIES GAS MONITORING SENSOR AND SYSTEM

ORIGIN OF THE INVENTION

Figure 1:
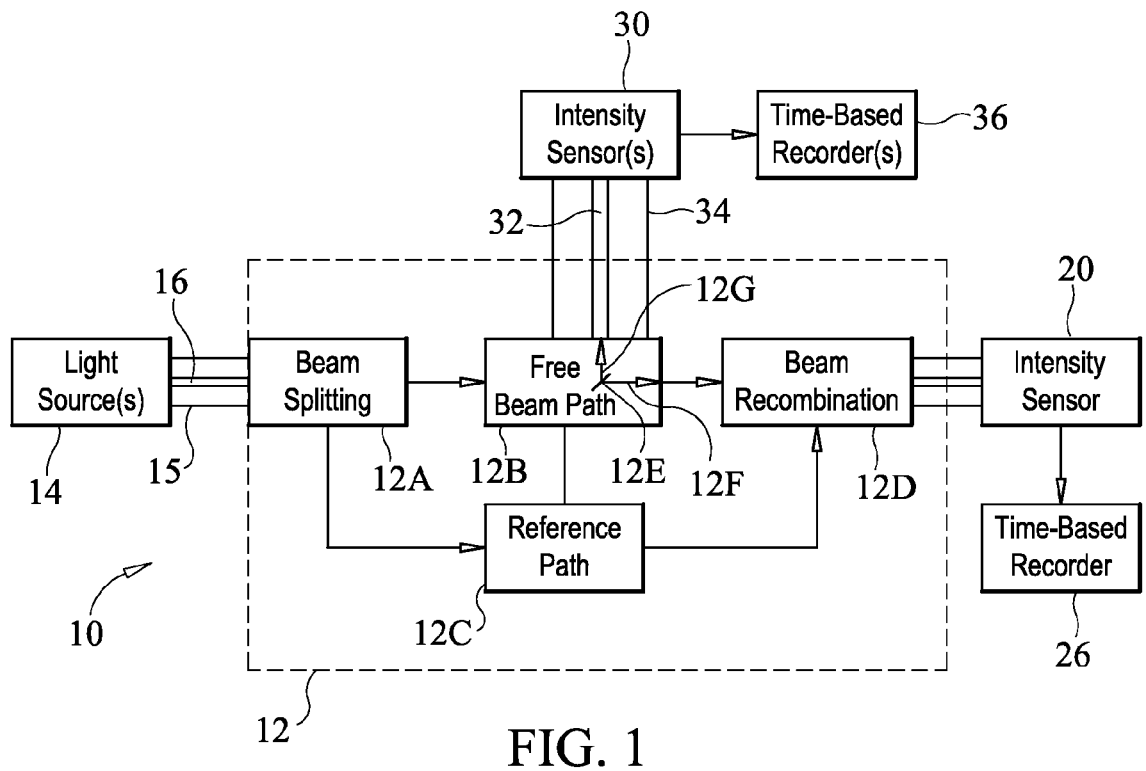

The invention described herein was made in the performance of work under a NASA contract and by an employee of the United States Government and is subject to the provisions of Public Law 96-517 (35 U.S.C §202) and may be manufactured and used by or for the Government for governmental purposes without the payment of any royalties thereon or therefore. In accordance with 35 U.S.C §202, the contractor elected not to retain title.

CROSS-REFERENCE TO RELATED PATENT APPLICATIONS

This patent application is co-pending with one related patent application entitled "OPTICAL SYSTEM AND METHOD FOR GAS DETECTION AND MONITORING", Ser. No. 12/336,260, filed Dec. 16, 2008, and owned by the same assignee as this patent application.

BACKGROUND OF THE INVENTION

1. Field of the Invention

This invention relates to gas detection and monitoring. More specifically, the invention is an optical-based sensor and system for monitoring a variety of gases particularly in vacuum environments such as space.

2. Description of the Related Art

In terms of near-term, long-distance space travel, missions to the Moon and Mars are likely possibilities. Lunar and longer-term Martian missions may require the capability to store cryogenic liquids in an unmanned state for long periods of time. Storage containers filled with a variety of materials such as cryogenic fluids, pressurized helium, or methane propellant, could be placed on the surface of another body in advance of a manned landing. Earth Departure Stages (EDS) for trips to the moon and Mars could be "parked" in orbit for several months with the tanks thereof being maintained in a filled state. A method for determining whether these pressurized systems are in a 'safe' (i.e., non-leaking) condition is needed before resources are allocated for a rendezvous with a space crew. Furthermore, during the course of a mission, it becomes critical to monitor the system's health to ensure that no leaks develop and/or discover them early after their occurrence so corrective action can be taken before the mission is endangered. Since different systems store a variety of gases or liquids, gas leaks of concern could involve a variety of gas species.

Since space environments are essentially vacuum environments, any leak detection and/or monitoring system/method must be capable of operating in a vacuum environment. In general, there are several methods to detect the presence of a gas in vacuum, but no off-the-shelf instrument is particularly well-suited for multiple gas species leak detection that can occur on various times scales and lead to pressure levels in the vicinity of the leak that span several orders of magnitude. High-vacuum gauges (ion gauges) are quite accurate at low pressures, but they are relatively fragile and their filaments can become damaged if operation is attempted above 1 milliTorr for any prolonged period of time. Furthermore, high-vacuum gauges generate heat that could ignite a leaking combustible propellant. Mass spectrometers can be large and are difficult to locate in space-limited or remote locations. In addition, their operation requires high-voltage, the presence of which is generally not desirable next to a liquid hydrogen or oxygen tank. Reactive coupons (e.g., palladium-catalyzed silicon carbide) are generally species specific and can severely outgas in a vacuum environment to the point of uselessness.

SUMMARY OF THE INVENTION

Accordingly, it is an object of the present invention to provide a sensor and system for monitoring a variety of gas species in an environment of interest.

Another object of the present invention is to provide a sensor and system for monitoring gas leaks in vacuum or space environments.

Other objects and advantages of the present invention will become more obvious hereinafter in the specification and drawings.

In accordance with the present invention, a gas monitoring sensor and system are provided. The system includes at least one light source for generating light energy having a corresponding wavelength. The system's sensor is based on an optical interferometer that receives light energy from each light source. The optical interferometer includes a free-space optical path disposed in an environment of interest where the light energy from each light source is introduced into the optical path. The system's sensor also includes an optical device disposed in the optical path. The optical device provides for at least partial transmission of the light energy and at least partial reflection of the light energy based upon the corresponding wavelength thereof. The optical device causes light energy of a first selected wavelength to continue traversing the optical path whereas light energy of at least one second selected wavelength is directed away from the optical path. The optical interferometer generates an interference between the light energy of the first selected wavelength so-traversing the optical path with the light energy at the corresponding wavelength incident on the optical interferometer. A first optical detector optically coupled to the optical interferometer is used to detect the interference. At least one second detector optically coupled to the optical interferometer is used to detect the light energy at the at least one second selected wavelength directed away from the optical path.

BRIEF DESCRIPTION OF THE DRAWING(S)

Figure 2:
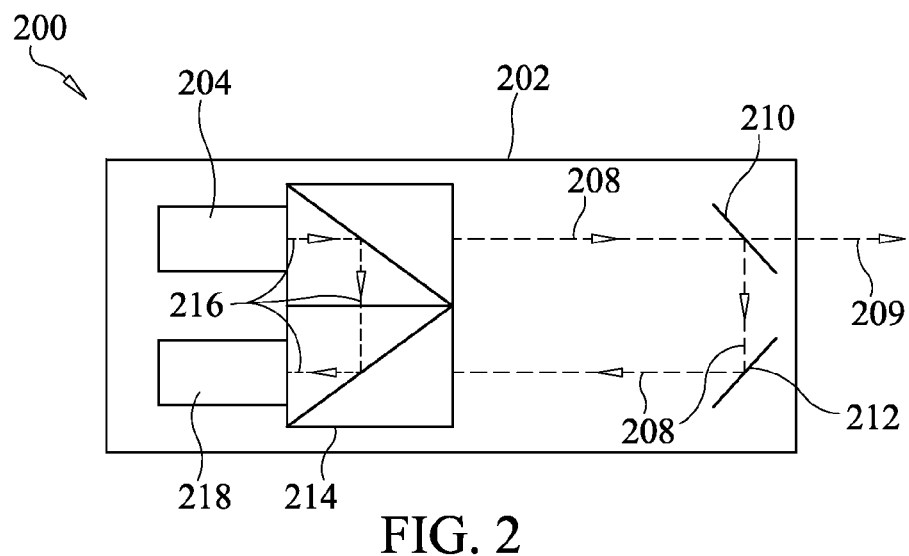

Other objects, features and advantages of the present invention will become apparent upon reference to the following description of the preferred embodiments and to the drawings, wherein corresponding reference characters indicate corresponding parts throughout the several views of the drawings and wherein:

FIG. 1 is a block diagram of a multi-species gas monitoring sensor and system in accordance with the present invention; and FIG. 2 is a schematic view of a Michelson solid-body optical interferometer configured as a sensor in accordance with an embodiment of the present invention.

DESCRIPTION OF THE PREFERRED EMBODIMENT(S)

Referring now to the drawings and more particularly to FIG. 1, a block diagram of a gas monitoring sensor and system in accordance with an embodiment of the present invention is shown and is referenced generally by numeral 10. By way of illustrative example, the present invention will be described for its use in monitoring the leakage of multiple species of gas into a non-gaseous vacuum environment. Monitoring will generally take place outside of a positive-pressure container that stores a gas (or liquid). For example, the container could be cryogenic liquid storage tank parked in a spatial orbit or deployed on a lunar or other planetary surface. In either of these situations, it is assumed that the environment surrounding the storage tank is a non-gaseous space environment.

At the heart of system 10 is a multi-species gas sensor 12 positioned where gas monitoring is of interest. Sensor 12 incorporates an optical interferometer that can be constructed in accordance with the operating principles associated with a Fabry-Perot interferometer, a Mach-Zehnder interferometer, or a Michelson interferometer. By way of a non-limiting example, a compact Michelson interferometer constructed in accordance with solid-body optics principles will be described later herein.

Regardless of the particular construction of the interferometer incorporated into sensor 12, the operating principles of the present invention remain the same. At the front end of sensor 12 of the illustrated embodiment, incoming light energy experiences beam splitting 12A in order to provide the light to a free beam path 12B and a reference path 12C. Free beam path 12B is an optical path defined by sensor 12 that passes through free space and is exposed to the surrounding environment of interest (e.g., the space environment at a position of interest near a storage tank such as a cryogenic liquid storage tank). Reference path 12C is an optical path defined within sensor 12 and is isolated from the surrounding environment so that the light energy incident thereon and traveling therealong remains undisturbed. At the end of free beam path 12B, the light energy passing therealong is combined with the light energy exiting reference path 12C at beam recombination 12D. The natural interference occurring from these two light beams serves as an interferometric output of sensor 12. Accordingly, elements 12A-12D of sensor 12 define an optical interferometer.

Sensor 12 includes additional capability as compared to a conventional optical interferometer. Specifically, positioned within free beam path 12B is an optical element, device or system 12E that possesses both optical transmission properties and optical reflectance properties where such properties are invoked predicated on the wavelength of the light energy impinging thereon. That is, optical device 12E allows some wavelength(s) of light energy to complete the traversal of free beam path 12B (as referenced by arrow 12F) while redirecting other wavelength(s) of light energy out of free beam path (as referenced by arrow 12G). Choices for optical device 12E include, but are not limited to, coated mirrors or glass, beam splitters, etc. Examples of various types of light energy as they relate to various species of gas monitoring will be described further below.

The light energy provided to sensor 12 originates at one or more light source(s) 14. While sensor 12 can be used with only one light source 14, a great advantage of the present invention is that sensor 12 is configured for simultaneous use with a plurality of sources 14 such that sensor 12 can be used to simultaneously monitor multiple gas species (e.g., simple gases that exist as unitary or binary molecules such as hydrogen, helium, carbon monoxide, carbon dioxide, water vapor, etc.; gas species that fluoresce in the presence of ultraviolet light such as organic or biological gas species; gas species whose rotational and translational molecular states are excited in the presence of infrared light such as hydrocarbons).

By way of example, several non-limiting types of light sources 14 will be described herein. When multiple light sources are used, their unique wavelength outputs could be merged or fused prior to being provided to sensor 12. Another option is to operate the multiple, unique-wavelength light sources on scheduled cycles so that, at any give moment, sensor 12 is only "processing" light energy from a single source. The choice and structure for providing the light energy to sensor 12 is not a limitation of the present invention.

In the illustrated embodiment, the light energy from source (s) 14 is transmitted (simultaneously or in cycles) to sensor 12 using a single-mode optical fiber 16. The single-mode fiber allows only one wave mode (e.g., the fundamental mode) to travel through the fiber. This maintains the coherence of the light. In this way, any interference generated by the optical interferometer incorporated in sensor 12 will occur in the single mode thereby making it easier to measure.

Since light energy transmitted in an optical fiber can be affected by vibrations, the orientation of fiber 16 can be fixed by a "housing" 18 that can be realized in a variety of ways as would be understood by one of ordinary skill in the art. Accordingly, the particular nature and/or configuration of housing 18 are not limitations of the present invention.

A variety of light sources 14 will now be described herein along with the type of gas species that could be monitored therewith. Regardless of the gas species of interest, it will generally be desirable to know how much gas is present. Thus, one measurement of interest is gas density in free beam path 12B as compared to reference path 12C. To monitor gas density, sensor 12 operates as an optical interferometer. To achieve this, one of the light sources 14 must be capable of generating a continuous beam of light with sufficient power to satisfy the operating principles of gas density monitoring. For example, light source 14 can be a continuous wave (CW) laser (e.g., a helium-neon laser). A CW laser outputs energy in a form that is similar to a standing wave. Sensor 12 splits the CW wave into two paths with one path being shifted relative to the other when there is interaction with the gas from a leak. When sensor 12 then brings the two paths back together in accordance with interferometric principles, interference occurs based on the relative optical phase difference between the two waves. Thus, for sensor 12 to operate in this interferometric capacity, optical device 12E must be configured to pass the wavelength(s) associated with the light energy from the CW laser. In this way, beam recombination 12D will generate the needed optical interference between light energy traversing free beam path 12B and reference path 12C. It is to be understood that the present invention is not limited to use with a CW laser as a light emitting diode (LED) might also be suitable for certain low-power applications.

As mentioned above, the output light energy generated by the interferometric attributes of sensor 12 is a natural interference between the light energy at the end of free beam path 12B and the light energy exiting reference path 12C. The intensity of this output light is detected at an intensity sensor 20 (e.g., a photodiode) that is coupled in an optical sense to sensor 12. For example, intensity sensor 20 can be coupled directly to interferometer 12 or located remotely with respect thereto. Given the harshness of space environments, it may be desirable to locate intensity sensor 20 in a protected environment. In such a case, a single-mode optical fiber 22 can be used to guide the (interference) light energy from sensor 12 to intensity sensor 20. Similar to optical fiber 16, a housing 24 can be used to fix the orientation of optical fiber 22.

Since the goal of system 10 is to monitor changes in gas levels, a time-based recorder 26 can be coupled to intensity sensor 20. Recorder 26 is any suitable data recording device/system capable of recording the sensed data over a time period of interest. Since the intensity data is indicative of an amount of a gas, recording this data over time in a leak detection application provides an indication of a leak's starting point in time, duration, and severity.

Since mere knowledge of an amount of gas is generally not sufficient to analyze a potential problem, system 10 and sensor 12 are also configured for gas species determination. System 10 and sensor 12 can be configured for one gas species determination, or the simultaneous (or near simultaneous) determination of multiple gas species. Since such determinations require interaction of light energy with the monitored environment but do not generally rely on interferometric principles, optical device 12E is positioned in free beam path 12B to "pick off" the light energy after an interaction occurs in free beam path 12B. Accordingly, optical device 12E is also configured to redirect the relevant wavelengths such that they exit free beam path 12B along exit path 12G.

The light energy exiting free beam path 12B is measured/monitored by intensity sensor(s) 30 (analogous to intensity sensor 20) and time-based recorder(s) 36 (analogous to recorder 26). The choice of intensity sensor(s) 30 will be predicated on the type of light energy that must be monitored as will be explained further below. A single-mode optical fiber 32 within a housing 34 can be used to transport light energy from/along path 12G to intensity sensor(s) 30. The light energy could be merged to include multiple wavelengths or the light energy could appear in cycles corresponding to the cycles of light energy supplied to sensor 12.

If sensor 10 and sensor 12 must be sensitive to simple unitary atom or binary molecule gases, light source(s) 14 can include a broadband (i.e., white) light source. In this case, intensity sensor(s) 30 could include linear CCD or CMOS arrays, designs of which are well understood in the art. When system 10 and sensor 12 must additionally or alternatively be sensitive to organic or biological gas species that fluoresce in ultraviolet light, light source(s) 14 can include an ultraviolet light source. In this case, intensity sensor(s) 30 could include an ultraviolet photodiode or a "blue" enhanced CCD array, designs of which are well understood in the art. Still further, when system 10 and sensor 12 must additionally or alternatively be sensitive to complex-molecule gas species such as hydrocarbons, light source(s) 14 can include an ultraviolet light source. In this case, intensity sensor(s) 30 can include a microbolometer, designs of which are well understood in the art.

Sensor 12 can optionally include an optical temperature sensor 40 positioned near free beam path 12B. As is known in the art, optical temperature sensors can be readily provided by an optical fiber configured to include a Bragg grating, a fiber switch, or a Fabry-Perot cavity. Although not shown, a separate light source and detector would be optically coupled to optical temperature sensor 40. Operational aspects associated with such optical temperature sensors are well understood in the art.

As mentioned above, the particular type of optical interferometer incorporated in sensor 12 is not a limitation of the present invention. One type of interferometer that lends itself to compact, solid-body optics construction is a Michelson interferometer. By way of example, a sensor embodiment of the present invention that includes a suitable solid body Michelson interferometer is illustrated in FIG. 2 and is referenced generally by numeral 200. Sensor 200 has a rigid planar base 202 with a number of optical components mounted thereon. Specifically, a first "gradient-index" (GRIN) lens 204 is coupled to a first beam splitter 206. Light enters sensor 200 via GRIN lens 204, i.e., via a single-mode optical fiber (not shown) coupled thereto. One output of beam splitter 206 starts a free beam path (i.e., the dashed-line path referenced by numeral 208) that traces a path to/between mirrors 210/212 and then on to a second beam splitter 214. One or both of mirrors 210 and 212 could be coated to reflect light energy wavelengths requiring interferometric operations, but transmit light energy wavelengths not requiring interferometric operations as described above. For example, just mirror 210 could be coated to transmit light energy not requiring interferometric operations. Such transmission could occur along an exit path 209 that is directed away from free beam path 208. Exit path 209 is analogous to exit path 12G described above.

Beam splitters 206 and 214 are configured and arranged to also define a reference path (i.e., the dotted-line path referenced by arrow 216) therethrough that is indicative of the light energy entering GRIN lens 204. Beam splitter 216 combines the light energy at the end of the interferometer's free beam path with the light on reference path 216. The naturally-interfering output light energy exits beam splitter 216 and is coupled to a second GRIN lens 218 where a single-mode optical fiber (not shown) can be coupled.

The advantages of the present invention are numerous. The sensor and system described herein can be used in vacuum environments (e.g., space) to detect/monitor gas presence, amounts and types over long time periods. The sensor and system are readily adapted to monitor multiple points simultaneously. The resulting data set can be used in manual or automated analysis schemes to comprehensively evaluate gas presence, amounts and types in an environment of interest. The sensor and system utilize simple yet rugged components that can withstand the rigors of a space deployment.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A gas monitoring system, comprising:
    at least one light source for generating light energy having a corresponding wavelength;
    an optical interferometer for receiving said light energy from each said light source, said optical interferometer including a free-space optical path disposed in an environment of interest wherein said light energy from each said light source is introduced into said free-space optical path;
    an optical device disposed in said free-space optical path and providing for at least partial transmission of said light energy and at least partial reflection of said light energy based upon said corresponding wavelength thereof, wherein said light energy of a first selected wavelength continues traversing said free-space optical path and wherein said light energy of at least one second selected wavelength is directed away from said free-space optical path;
    said optical interferometer generating an interference between said light energy of said first selected wavelength so-traversing said free-space optical path with said light energy at said corresponding wavelength incident on said optical interferometer;
    a first optical detector optically coupled to said optical interferometer for detecting said interference; and
    at least one second detector optically coupled to said optical interferometer for detecting said light energy at said at least one second selected wavelength directed away from said free-space optical path.

2. A gas monitoring system as in claim 1, further comprising a recording device coupled to said first optical detector for recording a temporal history of said interference.

3. A gas monitoring system as in claim 1, further comprising at least one recording device coupled to said at least one second optical detector for recording a temporal history of said light energy at said at least one second selected wavelength directed away from said free-space optical path.

4. A gas monitoring system as in claim 1, further comprising a single-mode optical fiber coupled between said optical interferometer and (i) each said light source, (ii) said first optical detector, and (iii) each said second optical detector.

5. A gas monitoring system as in claim 1, wherein said optical interferometer is selected from the group consisting of a Fabry-Perot interferometer, a Mach-Zehnder interferometer, and a Michelson interferometer.

6. A gas monitoring system as in claim 1, wherein said optical interferometer comprises a solid-body optical interferometer.

7. A gas monitoring system as in claim 1, wherein said at least one light source is selected from the group consisting of a continuous wave laser, a broadband light source, an ultraviolet light source, and an infrared light source.

8. A gas monitoring system as in claim 1, further comprising an optical temperature sensor disposed in proximity to said free-space optical path.

9. A gas monitoring system, comprising:
a plurality of light sources, each of said light sources generating light energy having a corresponding unique wavelength;
an optical interferometer for receiving said light energy from each of said light sources, said optical interferometer including (i) a free-space optical path disposed in an environment of interest wherein said light energy from each of said light sources is introduced into said free-space optical path, and (ii) a reference path wherein said light energy from each of said light sources is introduced therein and traverses therealong while being isolated from the environment of interest;
an optical device disposed in said free-space optical path and providing for at least partial transmission of said light energy and at least partial reflection of said light energy based upon said corresponding unique wavelength thereof, wherein said light energy of a first selected wavelength continues traversing said free-space optical path and wherein said light energy of at least one second selected wavelength is directed away from said free-space optical path;
said optical interferometer generating an interference between said light energy of said first selected wavelength so-traversing said free-space optical path with said light energy at said corresponding unique wavelength traveling along said reference path;
a first optical detector optically coupled to said optical interferometer for detecting said interference; and
at least one second detector optically coupled to said optical interferometer for detecting said light energy at said at least one second selected wavelength directed away from said free-space optical path.

10. A gas monitoring system as in claim 9, further comprising a recording device coupled to said first optical detector for recording a temporal history of said interference.

11. A gas monitoring system as in claim 9, further comprising at least one recording device coupled to said at least one second optical detector for recording a temporal history of said light energy at said at least one second selected wavelength directed away from said free-space optical path.

12. A gas monitoring system as in claim 9, further comprising a single-mode optical fiber coupled between said optical interferometer and (i) each said light source, (ii) said first optical detector, and (iii) each said second optical detector.

13. A gas monitoring system as in claim 9, wherein said optical interferometer is selected from the group consisting of a Fabry-Perot interferometer, a Mach-Zehnder interferometer, and a Michelson interferometer.

14. A gas monitoring system as in claim 9, wherein said optical interferometer comprises a solid-body optical interferometer.

15. A gas monitoring system as in claim 9, wherein said a plurality of light sources is selected from the group consisting of a continuous wave laser, a broadband light source, an ultraviolet light source, and an infrared light source.

16. A gas monitoring system as in claim 9, further comprising an optical temperature sensor disposed in proximity to said free-space optical path.

17. A gas monitoring system, comprising:
a plurality of light sources, each of said light sources generating light energy having a corresponding unique wavelength;
an optical interferometer for receiving said light energy from each of said light sources, said optical interferometer including (i) a free-space optical path disposed in an environment of interest wherein said light energy from each of said light sources is introduced into said free-space optical path, and (ii) a reference path wherein said light energy from each of said light sources is introduced therein and traverses therealong while being isolated from the environment of interest;
an optical device disposed in said free-space optical path and providing for at least partial transmission of said light energy and at least partial reflection of said light energy based upon said corresponding unique wavelength thereof, wherein said light energy of a first selected wavelength continues traversing said optical path and wherein said light energy of at least one second selected wavelength is directed away from said free-space optical path;
said optical interferometer generating an interference between said light energy of said first selected wavelength so-traversing said free-space optical path with said light energy at said corresponding unique wavelength traveling along said reference path;
an optical temperature sensor disposed in proximity to said free-space optical path;
a first optical detector optically coupled to said optical interferometer for detecting said interference;
at least one second detector optically coupled to said optical interferometer for detecting said light energy at said at least one second selected wavelength directed away from said free-space optical path; and
a single-mode optical fiber coupled between said optical interferometer and (i) each said light source, (ii) said first optical detector, and (iii) each said second optical detector.

18. A gas monitoring system as in claim 17, further comprising at least one recording device coupled to (i) said first optical detector for recording a temporal history of said interference, and (ii) said at least one second optical detector for recording a temporal history of said light energy at said at least one second selected wavelength directed away from said free-space optical path.

19. A gas monitoring system as in claim 17, wherein said optical interferometer is selected from the group consisting of a Fabry-Perot interferometer, a Mach-Zehnder interferometer, and a Michelson interferometer.

20. A gas monitoring system as in claim 17, wherein said optical interferometer comprises a solid-body optical interferometer.

21. A gas monitoring system as in claim 17, wherein said a plurality of light sources is selected from the group consisting of a continuous wave laser, a broadband light source, an ultraviolet light source, and an infrared light source.

22. A gas monitoring sensor, comprising:
   an optical interferometer for receiving light energy, said optical interferometer including a free-space optical path disposed in an environment of interest wherein said light energy is introduced into said free-space optical path;
   an optical device disposed in said free-space optical path and providing for at least partial transmission of said light energy and at least partial reflection of said light energy based upon a corresponding wavelength thereof, wherein said light energy of a first selected wavelength continues traversing said free-space optical path and wherein said light energy of at least one second selected wavelength is directed away from said free-space optical path; and
   said optical interferometer generating an interference between said light energy of said first selected wavelength so-traversing said free-space optical path with said light energy at said corresponding wavelength so-received at said optical interferometer.

23. A gas monitoring sensor as in claim 22, wherein said optical interferometer is selected from the group consisting of a Fabry-Perot interferometer, a Mach-Zehnder interferometer, and a Michelson interferometer.

24. A gas monitoring sensor as in claim 22, wherein said optical interferometer comprises a solid-body optical interferometer.

* * * * *